United States Patent [19]

Tiefenbrun et al.

[11] Patent Number: 5,372,585
[45] Date of Patent: Dec. 13, 1994

[54] INSTRUMENT AND ASSOCIATED METHOD FOR APPLYING BIOLOGICALLY EFFECTIVE COMPOSITION DURING LAPAROSCOPIC OPERATION

[76] Inventors: Jonathan Tiefenbrun, 62 Country Rd., Mamaronek, N.Y. 10543; Peter J. Wilk, 185 W. End Ave., New York, N.Y. 10023

[21] Appl. No.: 84,695

[22] Filed: Jun. 29, 1993

Related U.S. Application Data

[63] Continuation-in-part of Ser. No. 866,814, Apr. 9, 1992, Pat. No. 5,223,939.

[51] Int. Cl.$^5$ .................... A61M 31/00; A61B 17/36
[52] U.S. Cl. ........................ 604/59; 604/57; 606/15; 606/213
[58] Field of Search .................... 606/2, 7–10, 606/13–16, 213, 214; 604/21, 57, 59, 60, 61, 51; 128/DIG. 8; 607/89

[56] References Cited

U.S. PATENT DOCUMENTS

| | | |
|---|---|---|
| 1,609,640 | 12/1926 | Bell et al. . |
| 1,711,352 | 4/1929 | Jeffreys . |
| 3,203,455 | 8/1965 | Horahin . |
| 3,428,404 | 2/1969 | Ciancio . |
| 3,749,084 | 7/1978 | Cucchiara . |
| 4,073,293 | 2/1978 | Philips et al. . |
| 4,485,824 | 12/1984 | Koll . |
| 4,672,969 | 6/1987 | Dew ........................ 606/16 |
| 4,692,140 | 9/1987 | Olson . |
| 4,790,819 | 12/1988 | Li et al. . |
| 4,801,263 | 1/1989 | Clark . |
| 4,854,320 | 8/1989 | Dew et al. ............... 606/213 |
| 4,877,037 | 10/1989 | Ko et al. . |
| 4,929,246 | 5/1990 | Sinofsky ..................... 606/8 |
| 4,997,371 | 3/1991 | Fischer . |
| 5,071,417 | 12/1991 | Sinofsky ..................... 606/8 |
| 5,100,429 | 3/1992 | Sinofsky ................... 606/195 |
| 5,156,613 | 10/1992 | Sawyer .................... 606/213 |
| 5,207,670 | 5/1993 | Sinofsky ..................... 606/9 |
| 5,222,939 | 6/1993 | Tiefenbrun et al. . |
| 5,240,675 | 8/1993 | Wilk et al. ................. 606/15 |
| 5,254,113 | 10/1993 | Wilk ........................ 606/213 |
| 5,310,407 | 5/1994 | Casale ...................... 604/51 |

FOREIGN PATENT DOCUMENTS

| | | |
|---|---|---|
| 395472 | 3/1909 | France . |
| 619625 | 10/1935 | Germany . |
| 1627186 | 2/1991 | U.S.S.R. . |

*Primary Examiner*—Ralph A. Lewis
*Attorney, Agent, or Firm*—R. Neil Sudol; Henry D. Coleman

[57] ABSTRACT

A laparoscopic instrument comprises an elongate shaft, an applicator component on the shaft for applying a biologically active composition to a tissue surface inside a patient during a laparoscopic procedure, and a fiber optic laser beam transmission guide extending along the shaft from a proximal end to a distal end of the shaft. A laser source is operatively connected to the fiber optic guide at the proximal end of the shaft for generating a laser beam for transmission through the guide upon application of the biologically active composition to the tissue surface during the laparoscopic procedure. The applicator component includes, at the distal end of the shaft, a roller or a flexible cup-shaped receptacle which stores a predetermined amount of the biologically active composition and which deforms in response to a pressing of the shaft, to deposit the biologically active composition onto the tissue surface.

18 Claims, 3 Drawing Sheets

INSTRUMENT AND ASSOCIATED METHOD FOR APPLYING BIOLOGICALLY EFFECTIVE COMPOSITION DURING LAPAROSCOPIC OPERATION

CROSS REFERENCE TO A RELATED APPLICATION

This application is a continuation-in-part of U.S. patent application Ser. No. 866,814 filed Apr. 9, 1992, now U.S. Pat. No. 5,222,939.

BACKGROUND OF THE INVENTION

This invention relates to a laparoscopic instrument. More particularly, this invention relates to an instrument used during a laparoscopic operation for delivering or applying a biologically effective composition to a surface inside a patient. The substance may specifically take the form of a nontoxic biocompatible adhesive or a hemostatic substance.

Laparoscopy involves the piercing of the abdominal wall with a trocar and the insertion of a tubular cannula or trocar sleeve through the perforation. Various instruments may be inserted through the trocar sleeve to perform surgical operations inside the abdomen.

Generally, upon the disposition of the first trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Frequently, controlled amounts of biologically active or effective compositions, such as coagulating agents, are introduced into the patient's abdomen during a laparoscopic procedure. These compositions must be transferred to the abdominal cavity through the trocar ports or laparoscopic cannulas, like the instrumentation used. Generally, a predetermined amount of a composition is placed on a spatula or other conventional laparoscopic instrument, the distal end of which is then inserted into the patient's abdomen through a trocar port or cannula. This method is delicate and difficult insofar as the tip of the applicator instrument may contact the inner surface of the trocar port or insofar as the biologically active composition may be dropped or otherwise lost during transit to the surgical site.

OBJECTS OF THE INVENTION

An object of the present invention is to provide a laparoscopic instrument for facilitating the application of controlled amounts of biologically active or effective substances to surfaces of internal body organs or prosthetic elements such as patches (e.g., a hernia cover patch) inside a patient's abdomen during a laparoscopic operation.

A more particular object of the present invention is to provide a laparoscopic instrument for applying a biologically effective adhesive to a surface inside a patient during a laparoscopic procedure.

A further particular object of the present invention is to provide a laparoscopic instrument for applying a coagulating agent to a surface inside a patient during a laparoscopic procedure.

Yet another particular object of the present invention is to provide such a laparoscopic instrument which is inexpensive to make and easy to use.

SUMMARY OF THE INVENTION

A laparoscopic instrument for use in applying a biologically active composition such as a biocompatible surgical adhesive to an internal tissue surface of a patient comprises, in accordance with the present invention, an elongate shaft, an applicator component on the shaft for applying a biologically active composition to the tissue surface inside a patient during a laparoscopic procedure, and a fiber optic laser beam transmission guide extending along the shaft from a proximal end to a distal end of the shaft. A laser source is operatively connected to the fiber optic guide at the proximal end of the shaft for generating a laser beam for transmission through the guide upon application of the biologically active composition to the tissue surface during the laparoscopic procedure.

According to another feature of the present invention, the applicator component includes a longitudinally extending channel extending along the shaft, an elongate element in the channel and a duct extending along the shaft in parallel with the channel. The applicator component also includes a feeder element for feeding the biologically active composition through the duct to a distal end portion of the channel, whereby the elongate applicator element can engage the biologically active composition to apply the biologically active composition to a surface inside the patient. The elongate applicator element may take the from of a brush at the distal end of the instrument, while the feeder element takes the form of a syringe.

According to another, alternative, feature of the present invention, the applicator component includes a flexible receptacle attached to the shaft at the distal end thereof for temporarily storing a predetermined amount of the biologically active composition and for deforming in response to a pressing of the shaft, to deposit the biologically active composition onto the tissue surface.

In another alternative embodiment of the laparoscopic instrument, the applicator component includes a roller at the distal end of the instrument shaft.

A surgical method in accordance with the present invention comprises the steps of (a) providing a trocar, a trocar sleeve and a laparoscopic instrument including a fiber optic laser beam transmission guide, a biologically active composition, and an applicator component for applying the biologically active composition to in internal tissue surface of a patient, (b) using the trocar to form a perforation in an external body surface of a patient, (c) disposing the trocar sleeve in the perforation, (d) inserting the elongate shaft of the laparoscopic instrument through the trocar sleeve so that a distal end of the instrument protrudes into a body cavity of the patient while a proximal end of the instrument remains outside the patient, (e) manipulating the proximal end of the instrument, from outside the patient, to apply the biologically active composition to an internal tissue surface inside the body cavity of the patient, and (f) transmitting a laser beam along the transmission guide to impinge upon the biologically active composition applied to said tissue surface, to thereby harden the biologically active composition.

Generally, the biologically active composition is a biocompatible adhesive which is cured or sealed by electromagnetic radiation, particularly, but not limited to, the intense essentially monochromatic radiation of a laser. Such compositions are well known, for example, from U.S. Pat. No. 5,209,776.

Where the applicator component of the laparoscopic instrument includes a deformable cup-shaped receptacle at a distal end of an elongate shaft, the step of manipulating includes the step of manipulating the proximal end of the instrument, from outside the patient, to place the cup-shaped receptacle into contact with the tissue surface and to deform the receptacle so as to press the composition onto the tissue surface. The receptacle is subsequently removed from the tissue surface, whereupon the receptacle is reformed to resume its cup shape. At least a portion of the composition is maintained in a deposit on the tissue surface upon removal of the receptacle from the tissue surface.

Where the shaft of the laparoscopic instrument is hollow and includes a feeder element for delivering an amount of a biologically effective adhesive to the receptacle, the method further comprises the step of operating the feeder to transfer a quantity of the biologically active composition to the receptacle upon removal of the receptacle from the tissue surface, also comprising the step of again pressing the receptacle to a surgical site upon transfer of the quantity of the biologically active composition to the receptacle.

Where the laparoscopic instrument includes a roller at a distal end of an elongate shaft, the application of the biologically active composition includes the steps of manipulating the proximal end of the instrument, from outside the patient, to place the roller into contact with a biologically active composition on the tissue surface, and further manipulating the proximal end of the instrument, from outside the patient, to roll the roller along the tissue surface to spread the composition along the tissue surface.

Where the instrument shaft is hollow and a feeder is operatively connected to the shaft for delivering an amount of a biologically effective adhesive to the tissue surface, the method further comprises the step of operating the feeder to transfer a quantity of the biologically active composition to the tissue surface. In addition, the feeder may be configured to deposit the adhesive on the roller. Then the proximal end of the instrument is manipulated, from outside the patient, to roll the roller along the internal tissue surface of the patient.

A surgical method comprises, in accordance with a more particular conceptualization of the present invention, the steps of (i) providing a trocar, a trocar sleeve and a laparoscopic instrument including a deformable cup-shaped receptacle at a distal end of an elongate shaft, (ii) further providing a biologically active composition in the receptacle, (iii) using the trocar to form a perforation in an external body surface of a patient, (iv) disposing the trocar sleeve in the perforation, (v) inserting the elongate shaft, with the composition disposed in the receptacle, through the trocar sleeve so that a distal end of the instrument protrudes into a body cavity of the patient while a proximal end of the instrument remains outside the patient, (vi) manipulating the proximal end of the instrument, from outside the patient, to place the cup-shaped receptacle into contact with a tissue surface inside the body cavity and to deform the receptacle so as to press the composition onto the tissue surface, (vii) removing the receptacle from the tissue surface, (viii) upon removal of the receptacle from the tissue surface, reforming the receptacle to resume its cup shape, and (ix) maintaining at least a portion of the composition in a deposit on the tissue surface upon removal of the receptacle from the tissue surface.

Where the instrument includes a fiber optic laser beam transmission guide, this particular method further comprises the step of transmitting a laser beam through the fiber optic guide and directing the beam to impinge upon the composition on the tissue surface upon removal of the receptacle therefrom.

A surgical method comprises, in accordance with another more particular conceptualization of the present invention, the steps of (1) providing a trocar, a trocar sleeve and a laparoscopic instrument including a roller at a distal end of an elongate shaft, (2) using the trocar to form a perforation in an external body surface of a patient, (3) disposing the trocar sleeve in the perforation, inserting the elongate shaft, with the roller, through the trocar sleeve so that a distal end of the instrument protrudes into a body cavity of the patient while a proximal end of the instrument remains outside the patient, (4) manipulating the proximal end of the instrument, from outside the patient, to place the roller into contact with a biologically active composition on a tissue surface inside the body cavity, and (5) further manipulating the proximal end of the instrument, from outside the patient, to roll the roller along the tissue surface to spread the composition along the tissue surface.

A laparoscopic instrument and associated methodology in accordance with the present invention facilitate the application of controlled amounts of biologically active substances to surfaces of internal body organs or prosthetic elements such as patches (e.g., a hernia cover patch) inside a patient's abdomen during a laparoscopic operation. The instrument may be inexpensively fabricated and is easy to use.

DETAILED DESCRIPTION

Figure 1:
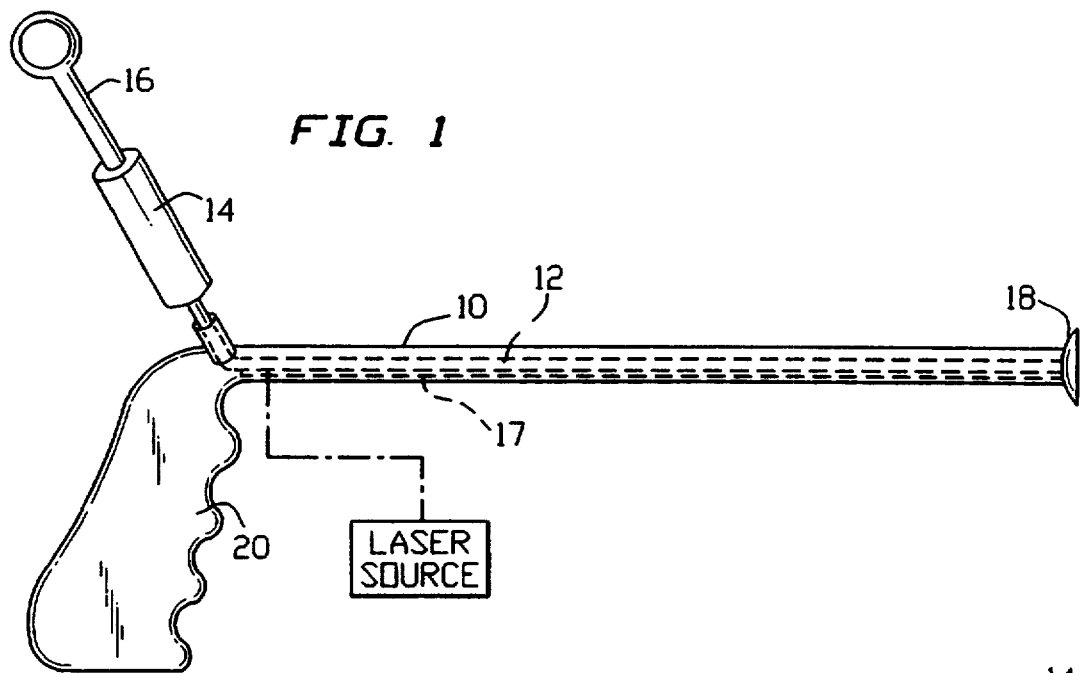
FIG. 1 is a schematic side elevational view of a laparoscopic adhesive delivery instrument in accordance with the present invention.

As illustrated in FIG. 1, a laparoscopic instrument for delivering a charge of a biologically effective, non-toxic and biocompatible adhesive to a desired location inside a patient's abdomen comprises an elongate hollow shaft 10 having a longitudinally extending channel or bore 12. A receptacle or reservoir in the form of a syringe 14 is operatively connected to shaft 10 at the proximal end thereof. Syringe 14 serves as a reservoir holding a predetermined amount of the adhesive and is provided with a manually actuatable plunger 16 for pressurizing the adhesive in the syringe to force the adhesive through channel 12 to a distal end of shaft 10.

At its distal end, shaft 10 is provided with a cup-shaped receptacle 18 for receiving and temporarily holding a charge of the adhesive and for releasing the charge upon engagement of the cup-shaped receptacle with a surface inside a patient. Cup-shaped receptacle 18 thus facilitates the delivery of a significantly controllable amount of adhesive to a desired location inside the patient. Receptacle 18 may be made of a flexible material having a memory so that it deforms upon forcible contact with a surface and subsequently returns to its cup shape.

Other feeder mechanisms may be substituted for syringe 14 and plunger 16. For example, a handle 20 at the proximal end of shaft 10 may define a reservoir for receiving a predetermined amount of the adhesive. In addition, a trigger like actuator (not shown) may be attached to shaft 10 and/or handle 20 for exerting a pressurizing force or a pumping action to move a charge of the adhesive through channel 12 to cup-shaped receptacle 18.

As further illustrated in FIG. 1, a fiber optic transmission guide 17 extends through shaft 10 from the proximal end to the distal end thereof. At the proximal end, fiber optic transmission guide 17 is operatively connected to a source or generator of laser radiation 19. At the distal end, fiber optic transmission guide 17 has an end face 21 (FIG. 2) inside receptacle 18. Upon the application of a charge of adhesive to a tissue surface inside a patient via a deformation of receptacle 18, laser source 19 is activated to transmit a laser beam along fiber optic transmission guide 17 and out through end face 21 to impinge upon the newly deposited adhesive. The laser beam serves to cure or solidify the adhesive, thereby bonding the adhesive to the tissue surface.

An adhesive suitable for use in accordance with the invention is disclosed in U.S. Pat. No. 5,209,776 the disclosure of which is hereby incorporated by reference.

An irrigation channel 23 extends through shaft 10 from a pressurizable irrigant reservoir 25 to enable a cleaning of receptacle 18 upon deposition of adhesive on a tissue surface inside a patient. The cleaning of receptacle 18 facilitates the use of fiber optic transmission guide 17 to cure the deposited adhesive.

Figure 3:
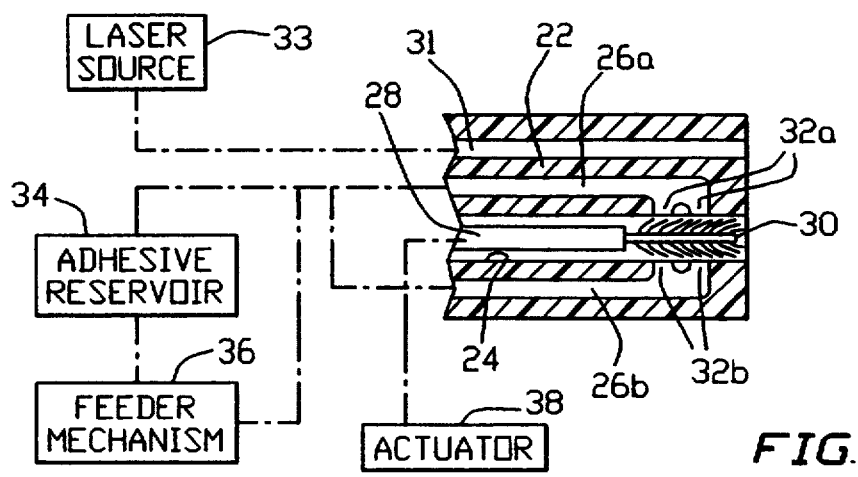
FIG. 3 is partially a block diagram and partially a cross-sectional view of another laparoscopic adhesive applicator or delivery instrument in accordance with the present invention.

As illustrated in FIG. 3, another laparoscopic instrument for delivering or applying a biologically effective, non-toxic and biocompatible adhesive to a desired surgical site inside a patient during a laparoscopic procedure includes an elongate hollow shaft 22 provided with a main channel 24 and a plurality of ancillary channels 26a and 26b. Main channel 24 is longitudinally traversed in part by a rod 28 provided at a distal end with an applicator brush 30. Ancillary channels 26a and 26b have openings 32a and 32b at the distal end of shaft 22.

Ancillary channels 26a and 26b communicate with a reservoir or receptacle 34 which contains a quantity of a biologically effective adhesive, i.e., a nontoxic composition capable of bonding biological tissues to one another and to prosthetic implant devices. A feeder mechanism 36 is operatively connected to reservoir or receptacle 34 for enabling the delivery of a controllable amount of the adhesive through channels 26a and 26b to a distal end of shaft 22.

Figure 6A:
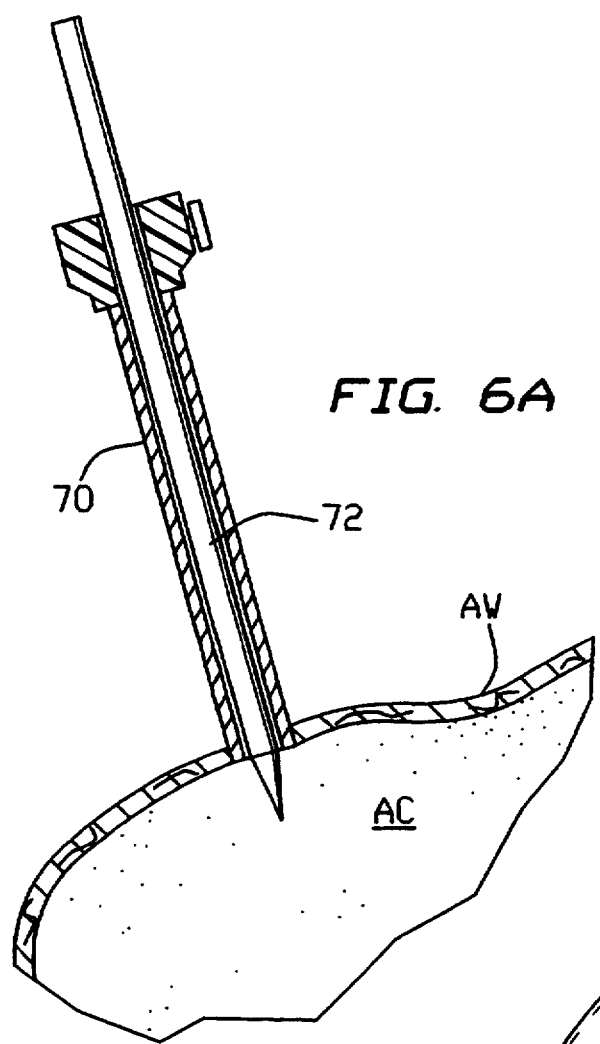
FIG. 6A is a schematic cross-sectional view showing insertion of a laparoscopic cannula or trocar sleeve through an abdominal wall.
Figure 6B:
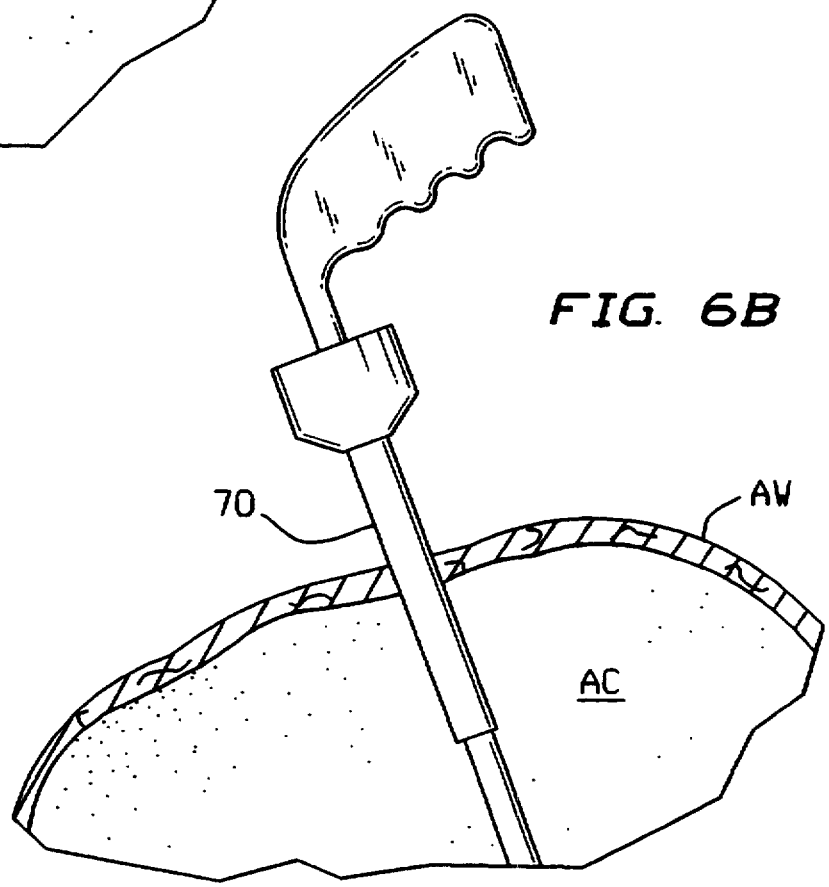
FIG. 6B is a schematic side elevational view of a deployed trocar sleeve through which a laparoscopic adhesive applicator in accordance with the present invention has been inserted.

Upon a feeding of adhesive to applicator brush 30 via channels 26a and 26b and openings 32a and 32b, rod 28 is pushed in the distal direction to eject the adhesive on the applicator brush. These steps are implemented upon an insertion of a distal end of shaft 22 into an abdominal cavity AC of a patient through a laparoscopic trocar sleeve 70 (FIGS. 6A and 6B).

An actuator 38 such as a handle is operatively connected to rod 28 for enabling an actuation of the rod from outside the patient to dispense the adhesive into the patient's abdomen.

Figure 2:
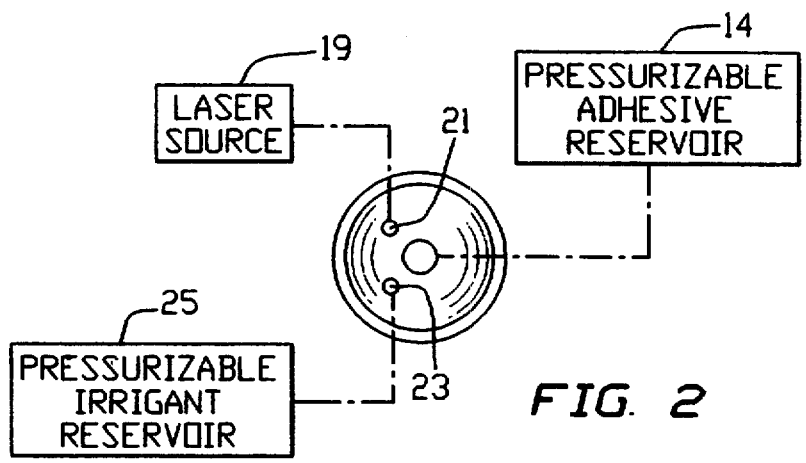
FIG. 2 is a schematic elevational view of a front end of the laparoscopic adhesive delivery instrument of FIG. 1.

Adhesives which may be utilized with the laparoscopic instruments of FIGS. 1 and 2 include cyanoacrylic compositions and fibrin glues or sealants such as TISSUCOL TM and BERIPLAST TM. The laparoscopic instruments of FIGS. 1 and 2 may each be provided with two reservoirs at a proximal end for separately holding two different chemical components, as well as two longitudinally extending feed channels for enabling a mixing of the two compositions at a distal end of the respective instrument to generate a chemical reaction producing an adhesive composition which will harden and fixate within a characteristic predetermined interval.

As further illustrated in FIG. 3, a fiber optic transmission guide 31 extends through shaft 22 from the proximal end to the distal end thereof. At the proximal end, fiber optic transmission guide 31 is operatively connected to a source or generator of laser radiation 33. Upon the application of a charge of adhesive to a tissue surface inside a patient via applicator brush 30, laser source 33 is activated to transmit a laser beam along fiber optic transmission guide 31 to impinge upon the newly deposited adhesive. The laser beam serves to enhance the bonding of the adhesive to the tissue surface. As discussed in U.S. Pat. No. 5,209,776, a dye mixed in with the adhesive absorbs the laser energy and induces the curing of the adhesive compound.

Figure 4:
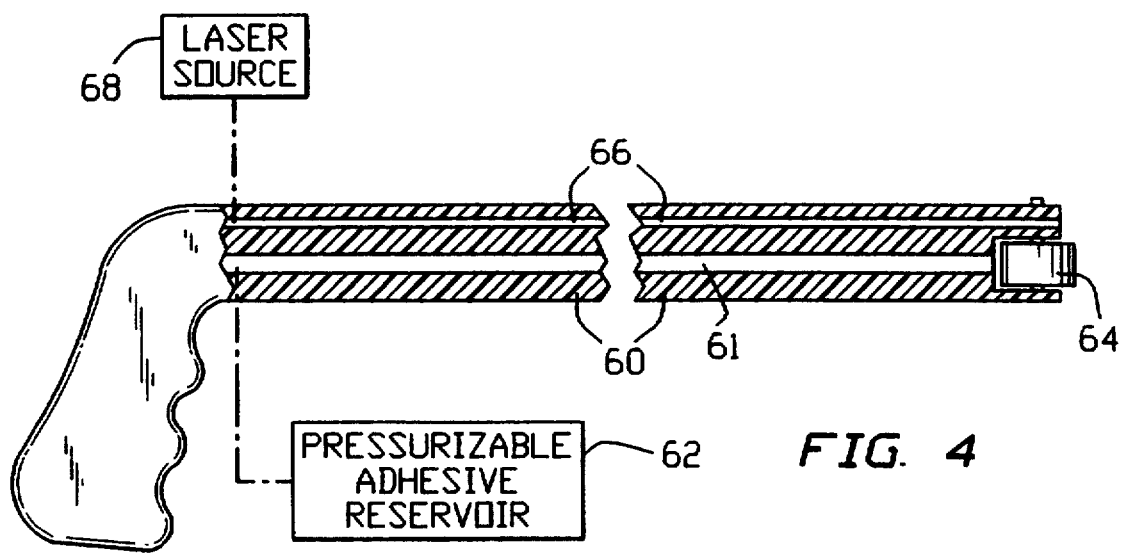
FIG. 4 is essentially schematic longitudinal cross-sectional view of yet another laparoscopic adhesive applicator or delivery instrument in accordance with the present invention.

As shown in FIG. 4, another laparoscopic instrument for applying a biological glue or adhesive to a tissue surface inside a patient during a laparoscopic procedure comprises a shaft 60 having a longitudinally extending channel 61 for transfering or delivering the adhesive from a reservoir 62 to a proximal side of a roller 64 rotatably fastened to the distal end of shaft 60. Shaft 60 is further provided with a longitudinally extending fiber optic transmission guide 66 operatively connected at a proximal end to a laser source 68. Upon application of adhesive to a tissue surface via roller 64, source 68 is activated to transmit a laser along fiber optic guide 66 to the deposited adhesive.

In using the instrument of FIG. 4, and the other instruments disclosed herein, a distal end portion of the instrument is inserted into the abdominal cavity AC (FIGS. 6A and 6B) of the patient via a trocar sleeve 70 which is itself disposed in an abdominal wall AW of the patient upon the piercing of the wall with a trocar 72. A proximal end of the instrument is manipulated, from outside the patient, to place the roller into contact with the biologically compatible or active adhesive on a tissue surface inside the body cavity. Generally, the adhesive is deposited on the roller and the instrument is manipulated from outside the patient to roll the roller along the tissue surface to transfer the adhesive from the roller to the tissue surface and to spread the composition along the tissue surface.

Figure 5:
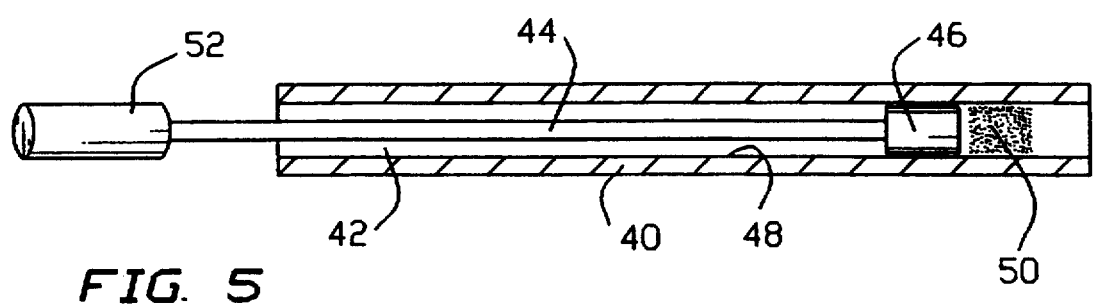
FIG. 5 is a schematic longitudinal cross-sectional view of a laparoscopic instrument for delivering or applying a charge of a hemostatic agent, in accordance with the present invention.

As illustrated in FIG. 5, a laparoscopic instrument for delivering a predetermined amount of a hemostatic substance or coagulating agent inside a patient during a laparoscopic procedure includes an elongate hollow shaft 40 provided with a longitudinally extending channel 42 and an ejector rod 44 at least partially disposed inside the channel. Ejector rod 44 is provided at a distal end with a piston 46 which engages a cylindrical inner wall 48 of shaft 40.

Disposed inside shaft 40 distally of piston 46 is a predetermined charge 50 of a coagulating agent such as avatine. Avatine charge 50 is ejected by a distally directed stroke of rod 44 upon an insertion of a distal end of shaft 40 into the abdomen of a patient through a laparoscopic cannula.

A handle type actuator 52 is operatively connected to ejector rod 44 for enabling an actuation of the rod from outside the patient to precisely eject or dispense the coagulating substance into the patient's abdomen at a desired location.

The laparoscopic instrument of FIG. 3 may be prepackaged and disposable upon the delivery of charge 50 to a surgical site. To that end a plug (not shown) may be inserted in the distal end of channel 42 to hold charge 50 during shipping and storage prior to use.

Although the invention has been described in terms of particular embodiments and applications, one of ordinary skill in the art, in light of this teaching, can generate additional embodiments and modifications without departing from the spirit of or exceeding the scope of the claimed invention. For example, substances other than an adhesive or a hemostatic factor may be precisely and controlled delivered to a desired surgical site inside a patient during a laparoscopic procedure using instruments in accordance with the present invention.

In addition, the dispensing action may effectuated equivalently by controlling a valve at an outlet of a pressurized reservoir of adhesive or other fluidic substance.

Accordingly, it is to be understood that the drawings and descriptions herein are preferred by way of example to facilitate comprehension of the invention and should not be construed to limit the scope thereof.

What is claimed is:

1. A surgical method comprising the steps of:
    providing a trocar, a trocar sleeve and a laparoscopic instrument including an elongate shaft having a distal end and a proximal end, a fiber optic laser beam transmission guide connected to and extending along said shaft between said proximal end and said distal end, a biologically active composition held on said shaft at said distal end, and applicator means connected to said shaft for applying the biologically active composition to an internal tissue surface of a patient;
    using said trocar to form a perforation in an abdominal wall of a patient;
    disposing said trocar sleeve in said perforation;
    inserting said elongate shaft through said trocar sleeve so that said distal end protrudes into an abdominal cavity of the patient while said proximal end remains outside said patient;
    manipulating said proximal end of said elongate shaft, from outside the patient, to operate said applicator means to apply said biologically active composition to an internal tissue surface inside the abdominal cavity of the patient; and
    transmitting a laser beam along said transmission guide to impinge upon the biologically active composition applied to said tissue surface, to thereby harden said biologically active composition.

2. The method defined in claim 1 wherein said applicator means includes a deformable cup-shaped receptacle at said distal end of said elongate shaft, said step of manipulating including the steps of:
    manipulating said proximal end of said elongate shaft, from outside the patient, to place said cup-shaped receptacle into contact with said tissue surface and to deform said receptacle so as to press said composition onto said tissue surface;
    removing said receptacle from said tissue surface;
    upon removal of said receptacle from said tissue surface, reforming said receptacle to resume its cup shape; and
    maintaining at least a portion of said composition in a deposit on said tissue surface upon removal of said receptacle from said tissue surface.

3. The method defined in claim 2 wherein said shaft is hollow and wherein feeder means are operatively connected to said shaft at said proximal end for delivering an amount of a biologically effective adhesive to said receptacle via said shaft, further comprising the step of operating said feeder means to transfer a quantity of said biologically active composition to said receptacle upon removal of said receptacle from said tissue surface, also comprising the step of again pressing said receptacle to a surgical site upon transfer of said quantity of said biologically active composition to said receptacle.

4. The method defined in claim 1 wherein said means for applying includes a roller at a distal end of an elongate shaft, said step of manipulating including the steps of:
    manipulating said proximal end of said instrument, from outside the patient, to place said roller into contact with a biologically active composition on said tissue surface; and
    further manipulating said proximal end of said instrument, from outside the patient, to roll said roller along said tissue surface to spread said composition along said tissue surface.

5. The method defined in claim 4 wherein said shaft is hollow and wherein feeder means are operatively connected to said shaft at said proximal end for delivering an amount of a biologically effective adhesive to said tissue surface via said shaft, further comprising the step of operating said feeder means to transfer a quantity of said biologically active composition to said tissue surface.

6. The method defined in claim 5 wherein said step of operating said feeder means includes the steps of depositing said adhesive on said roller and manipulating said proximal end of said instrument, from outside the patient, to roll said roller along said tissue surface.

7. A surgical method comprising the steps of:

providing a trocar, a trocar sleeve and a laparoscopic instrument including a deformable cup-shaped receptacle at a distal end of an elongate shaft;

further providing a biologically active composition in said receptacle;

using said trocar to form a perforation in an external body surface of a patient;

disposing said trocar sleeve in said perforation;

inserting said elongate shaft, with said composition disposed in said receptacle, through said trocar sleeve so that a distal end of said instrument protrudes into a body cavity of the patient while a proximal end of said instrument remains outside said patient;

manipulating said proximal end of said instrument, from outside the patient, to place said cup-shaped receptacle into contact with a tissue surface inside said body cavity and to deform said receptacle so as to press said composition onto said tissue surface;

removing said receptacle from said tissue surface;

upon removal of said receptacle from said tissue surface, reforming said receptacle to resume its cup shape; and maintaining at least a portion of said composition in a deposit on said tissue surface upon removal of said receptacle from said tissue surface.

8. The method defined in claim 7 wherein said instrument includes a fiber optic laser beam transmission guide extending along said shaft from said proximal end to said distal end, further comprising the step of transmitting a laser beam through said guide and directing said beam to impinge upon said composition on said tissue surface upon removal of said receptacle therefrom.

9. The method defined in claim 7 wherein said shaft is hollow and wherein feeder means are operatively connected to said shaft at said distal end for delivering an amount of a biologically effective adhesive to said receptacle via said shaft, further comprising the step of operating said feeder means to transfer a quantity of said biologically active composition to said receptacle upon removal of said receptacle from said tissue surface, also comprising the step of again pressing said receptacle to a surgical site upon transfer of said quantity of said biologically active composition to said receptacle.

10. A surgical method comprising the steps of:
providing a trocar, a trocar sleeve and a laparoscopic instrument including a roller at a distal end of an elongate shaft;

using said trocar to form a perforation in an abdominal wall of a patient;

disposing said trocar sleeve in said perforation;

inserting said elongate shaft, with said roller, through said trocar sleeve so that a distal end of said instrument protrudes into an abdominal cavity of the patient while a proximal end of said instrument remains outside said patient;

manipulating said proximal end of said instrument, from outside the patient, to place said roller into contact with a biologically active composition on a tissue surface inside said abdominal cavity; and further manipulating said proximal end of said instrument, from outside the patient, to roll said roller along said tissue surface to spread said composition along said tissue surface.

11. The method defined in claim 10 wherein said shaft is hollow and wherein feeder means are operatively connected to said shaft at said proximal end for delivering an amount of a biologically effective adhesive to said tissue surface via said shaft, further comprising the step of operating said feeder means to transfer a quantity of said biologically active composition to said tissue surface.

12. The method defined in claim 11 wherein said step of operating said feeder means includes the steps of depositing said adhesive on said roller and manipulating said proximal end of said instrument, from outside the patient, to roll said roller along said tissue surface.

13. The method defined in claim 10 wherein said instrument includes a fiber optic laser beam transmission guide extending along said shaft from said proximal end to said distal end, further comprising the step of transmitting a laser beam through said guide and directing said beam to impinge upon said composition on said tissue surface upon spreading of said composition on said tissue surface by said roller.

14. A laparoscopic instrument comprising:
an elongate shaft having a distal end and a proximal end;

means on said shaft at least at said distal end thereof for applying a biologically active composition to a tissue surface inside a patient during a laparoscopic procedure;

a fiber optic laser beam transmission guide extending along said shaft from said proximal end to said distal end; and a laser source operatively connected to said guide at said proximal end of said shaft for generating a laser beam for transmission through said guide upon application of said biologically active composition to said tissue surface during said laparoscopic procedure, said means for applying including flexible receptacle means attached to said shaft at said distal end thereof for temporarily storing a predetermined amount of said biologically active composition and for deforming in response to a pressing of said shaft, to deposit said biologically active composition onto said tissue surface.

15. A laparoscopic instrument comprising:
an elongate substantially rigid shaft having a distal end and a proximal end;

means on said shaft at least at said distal end thereof for applying a biologically active composition to a tissue surface inside a patient during a laparoscopic procedure, said means for applying including a roller rotatably mounted to said shaft at said distal end thereof;

a fiber optic laser beam transmission guide extending along said shaft from said proximal end to said distal end; and a laser source operatively connected to said guide at said proximal end of said shaft for generating a laser beam for transmission through said guide upon application of said biologically active composition to said tissue surface during said laparoscopic procedure.

16. A laparoscopic instrument comprising:
an elongate shaft having a distal end and a proximal end;

means on said shaft at least at said distal end thereof for applying a biologically active composition to a tissue surface inside a patient during a laparoscopic procedure;

a fiber optic laser beam transmission guide extending along said shaft from said proximal end to said distal end; and a laser source operatively connected to said guide at said proximal end of said shaft for generating a laser beam for transmission through said guide upon application of said biologically active composition to said tissue surface during said laparoscopic procedure, said means for applying including a longitudinally extending channel extending along said shaft, an applicator brush in said channel and a duct extending along said shaft in parallel with said channel, said means for applying also including feeder means for feeding said biologically active composition through said duct to a distal end portion of said channel, whereby said applicator element can engage said biologically active composition to apply said biologically active composition to a surface inside the patient.

17. The instrument defined in claim 16 wherein said biologically active composition is a biologically effective adhesive.

18. The instrument defined in claim 16 wherein said feeder means includes a syringe.

* * * * *